United States Patent
Fenster et al.

(10) Patent No.: US 8,696,561 B2
(45) Date of Patent: Apr. 15, 2014

(54) LEEP SAFETY GUARD

(75) Inventors: Tamatha Britt Fenster, New York, NY (US); Harold Irwin Sussman, Scarsdale, NY (US)

(73) Assignee: Tamatha Britt Fenster, New York, NY (US)

(*) Notice: Subject to any disclaimer, the term of this patent is extended or adjusted under 35 U.S.C. 154(b) by 142 days.

(21) Appl. No.: 13/042,941

(22) Filed: Mar. 8, 2011

(65) Prior Publication Data

US 2011/0245618 A1    Oct. 6, 2011

Related U.S. Application Data

(60) Provisional application No. 61/320,026, filed on Apr. 1, 2010.

(51) Int. Cl.
*A61B 1/32* (2006.01)

(52) U.S. Cl.
USPC .......................................................... 600/221

(58) Field of Classification Search
USPC ................................................. 600/185–235
See application file for complete search history.

(56) References Cited

U.S. PATENT DOCUMENTS

| | | | |
|---|---|---|---|
| 471,647 A | 3/1892 | Magoris | |
| 2,672,859 A | 3/1954 | Jones | |
| 3,841,317 A * | 10/1974 | Awais | 600/203 |
| 3,870,036 A | 3/1975 | Fiore | |
| 3,943,916 A | 3/1976 | Vadas | |
| 5,063,908 A | 11/1991 | Collins | |
| 5,167,222 A | 12/1992 | Schinkel et al. | |
| 5,293,863 A * | 3/1994 | Zhu et al. | 600/214 |
| 5,324,288 A | 6/1994 | Billings et al. | |
| 5,392,764 A | 2/1995 | Swanson et al. | |
| 5,394,863 A | 3/1995 | Sanford et al. | |
| 5,458,595 A * | 10/1995 | Tadir et al. | 606/15 |
| 5,554,159 A | 9/1996 | Fischer | |
| 5,676,663 A | 10/1997 | Kim | |
| 5,716,329 A | 2/1998 | Dieter | |
| 5,743,852 A * | 4/1998 | Johnson | 600/207 |
| 5,785,648 A * | 7/1998 | Min | 600/206 |
| 5,846,249 A | 12/1998 | Thompson | |
| 5,916,150 A | 6/1999 | Sillman | |
| 6,036,638 A | 3/2000 | Nwawka | |
| 6,120,438 A | 9/2000 | Rizvi | |
| 6,258,024 B1 * | 7/2001 | van Der Weegen | 600/115 |
| 6,280,379 B1 | 8/2001 | Resnick | |
| 6,302,853 B1 | 10/2001 | Sak | |

(Continued)

*Primary Examiner* — Jan Christopher Merene
*Assistant Examiner* — Steven Cotroneo
(74) *Attorney, Agent, or Firm* — Notaro, Michalos & Zaccaria P.C.

(57) ABSTRACT

A guard and guide apparatus and method is used with a speculum having jaws in a vagina to define a passage toward a cervix at an end of the vagina. The guard and guide apparatus has a guard body movable into the passage, the guard body having sides, a top and a bottom defining a tunnel toward the cervix for preventing contact between a probe and walls of the vagina. Flexible cervix panels are at the inner end of the guard body and extend toward the fornix of the cervix for covering the fornix to protect it from contact by the probe. A support fulcrum is provided in the guard body tunnel at a location between inner and outer ends of the guard body for supporting the probe handle to help a practitioner hold the probe handle steady and aim the probe accurately to a selected location on the cervix.

12 Claims, 8 Drawing Sheets

(56) References Cited

U.S. PATENT DOCUMENTS

| | | | |
|---|---|---|---|
| 6,364,832 B1 * | 4/2002 | Propp | 600/220 |
| 6,371,968 B1 * | 4/2002 | Kogasaka et al. | 606/190 |
| 6,379,299 B1 | 4/2002 | Borodulin et al. | |
| 6,394,950 B1 | 5/2002 | Weiss | |
| 6,432,048 B1 | 8/2002 | Francois | |
| 6,712,761 B2 * | 3/2004 | Borodulin et al. | 600/184 |
| 6,749,563 B2 * | 6/2004 | Stihl | 600/196 |
| 6,902,530 B1 | 6/2005 | Planka | |
| 7,452,329 B2 * | 11/2008 | Bastia et al. | 600/184 |
| 7,594,888 B2 * | 9/2009 | Raymond et al. | 600/219 |
| 8,043,212 B1 * | 10/2011 | Bae et al. | 600/215 |
| 2005/0070765 A1 * | 3/2005 | Abdelgany et al. | 600/214 |
| 2009/0099422 A1 * | 4/2009 | George | 600/214 |

* cited by examiner

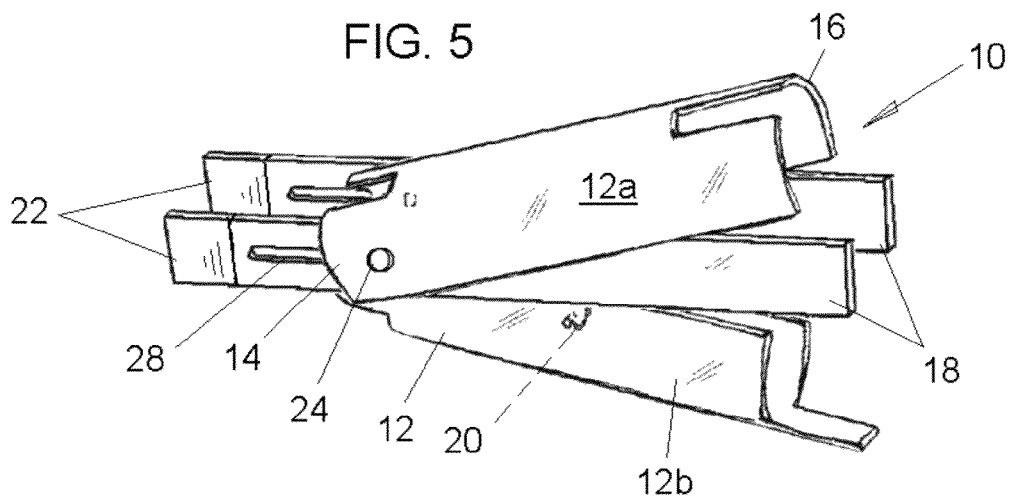
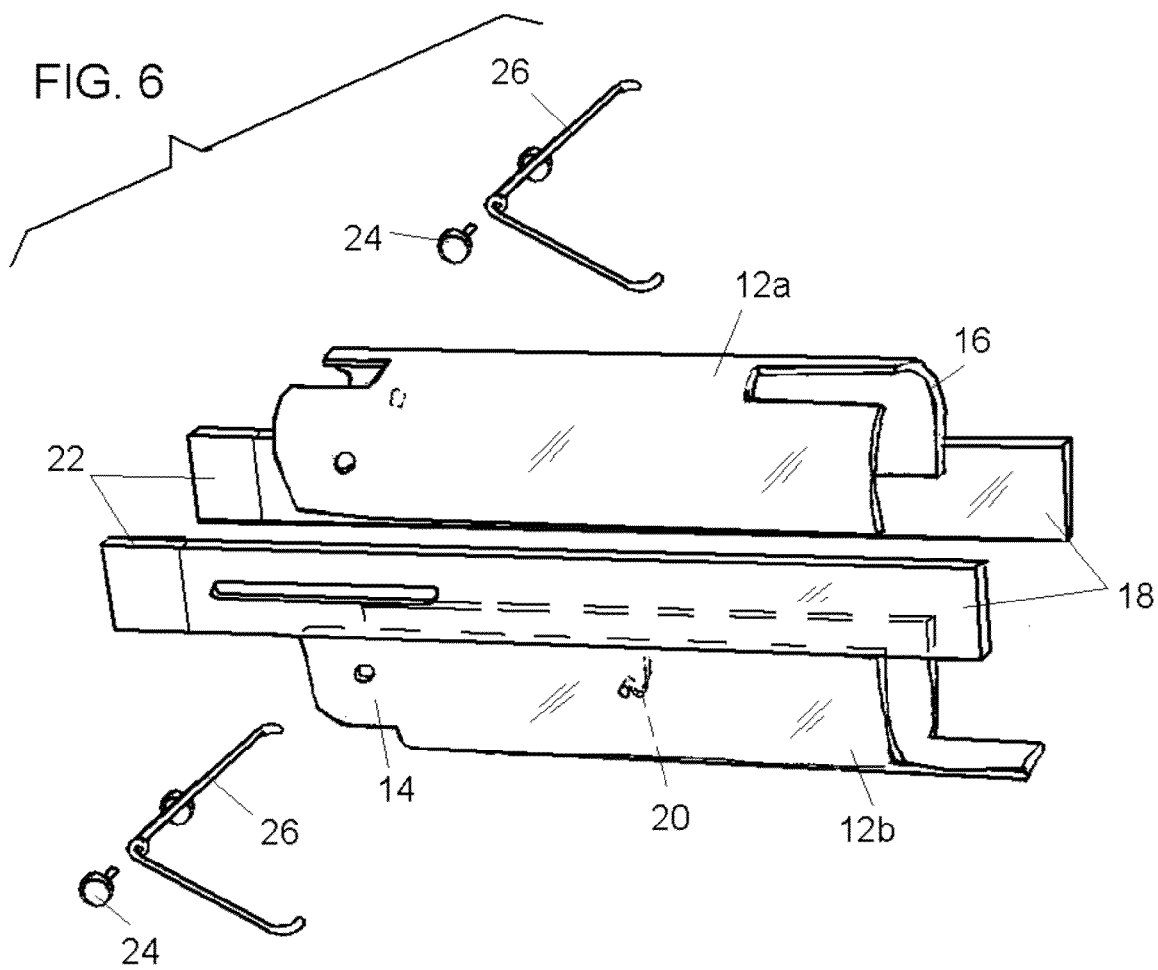

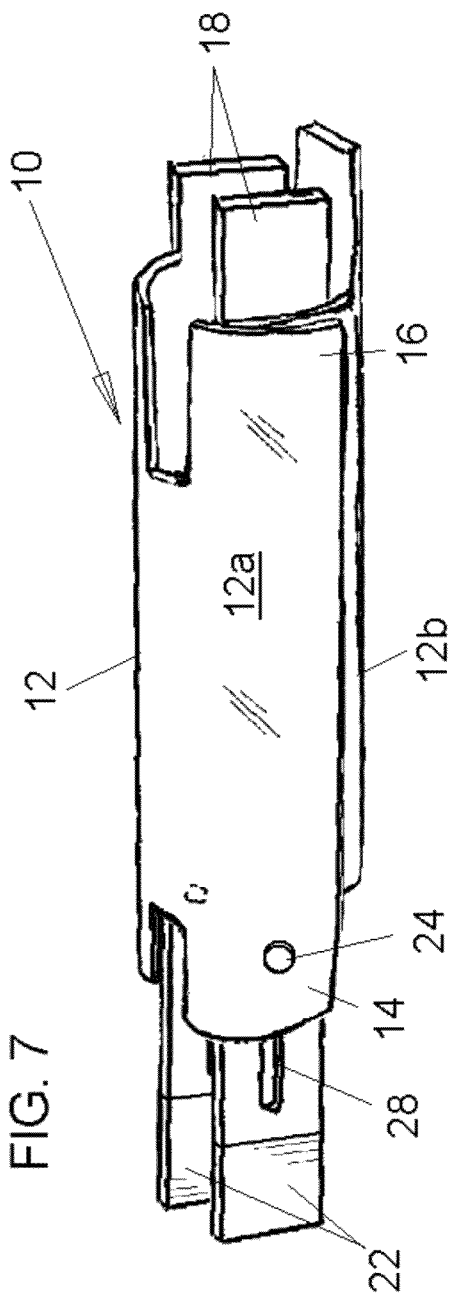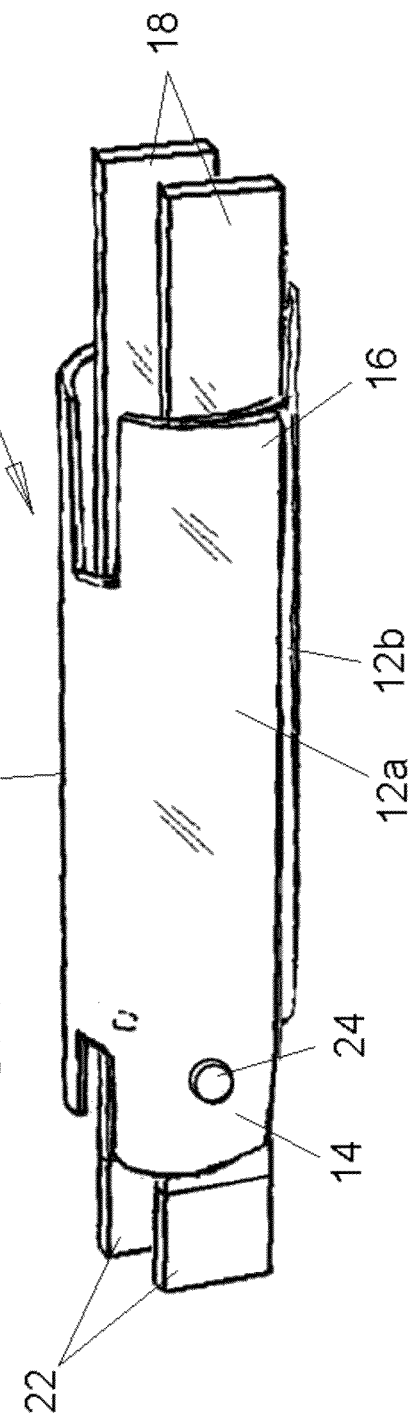

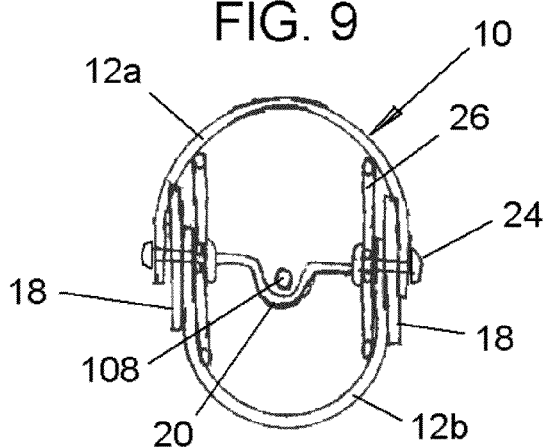
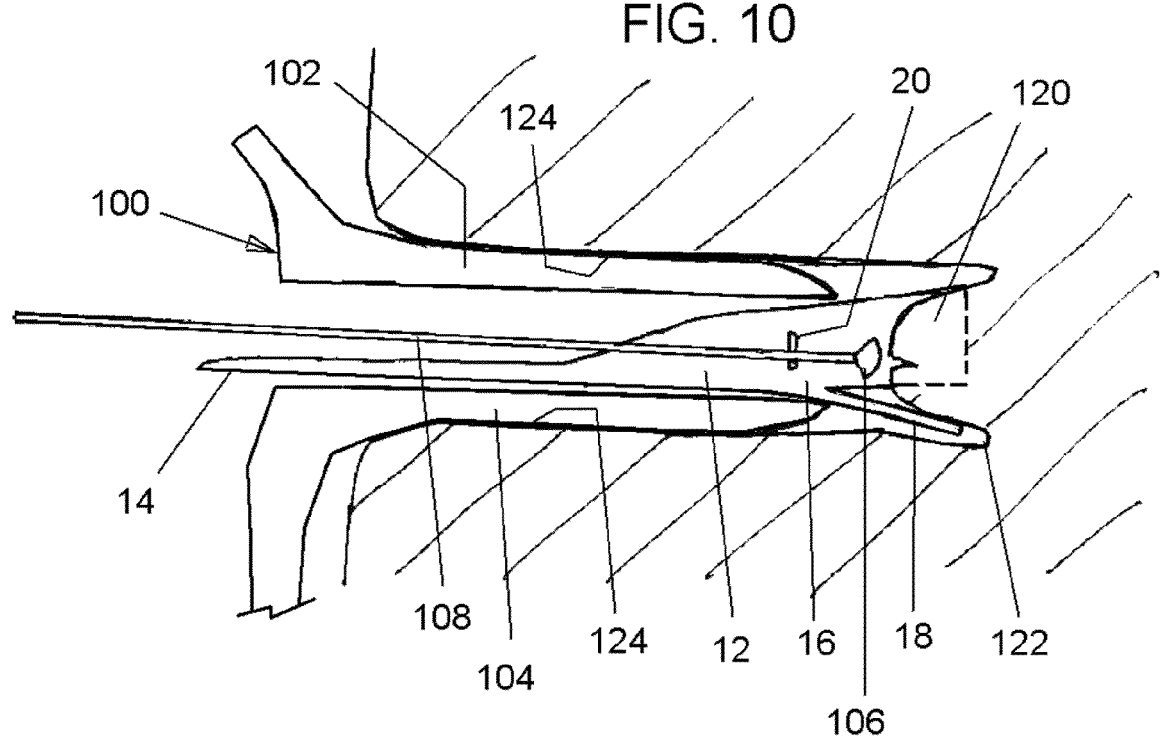

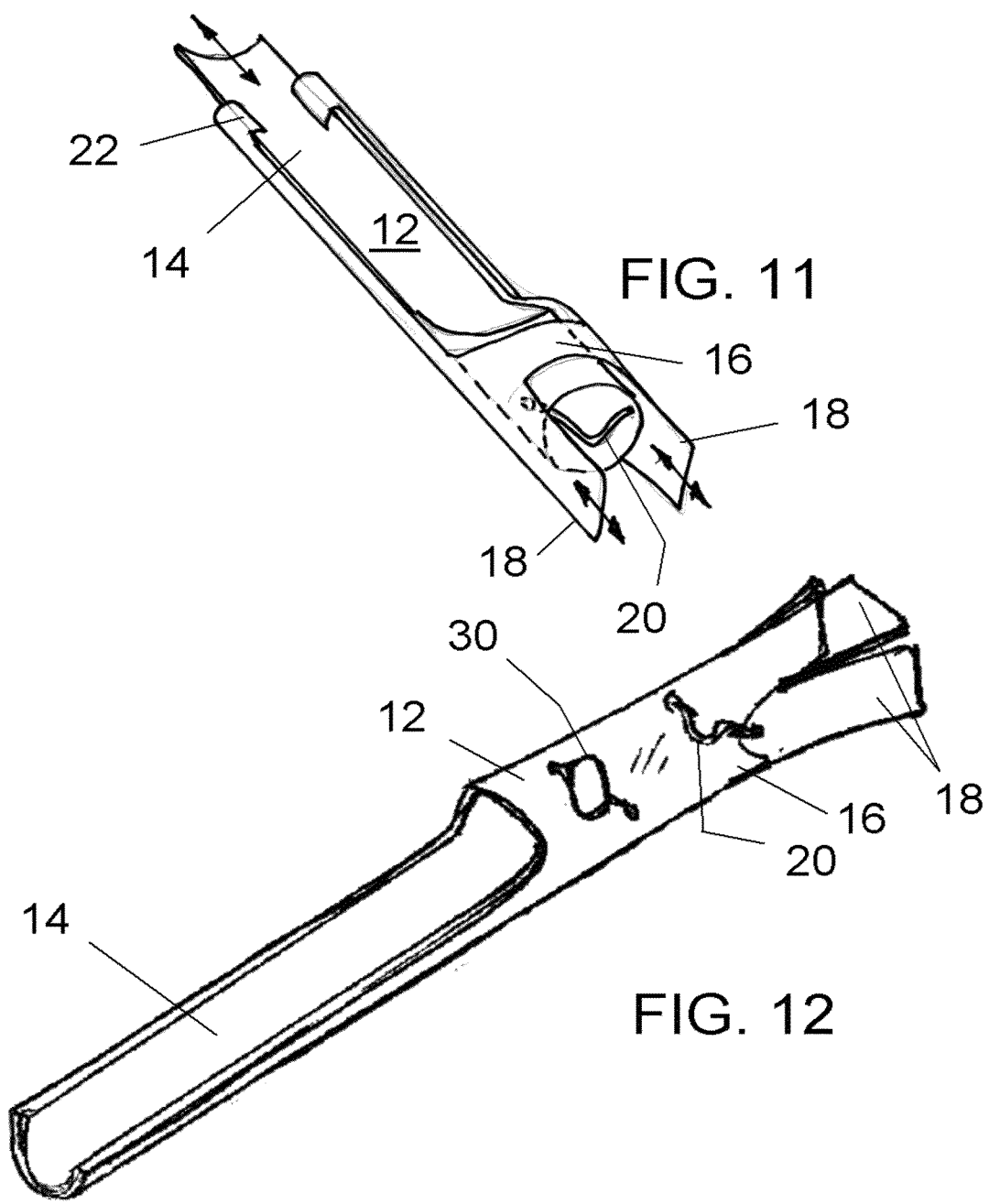

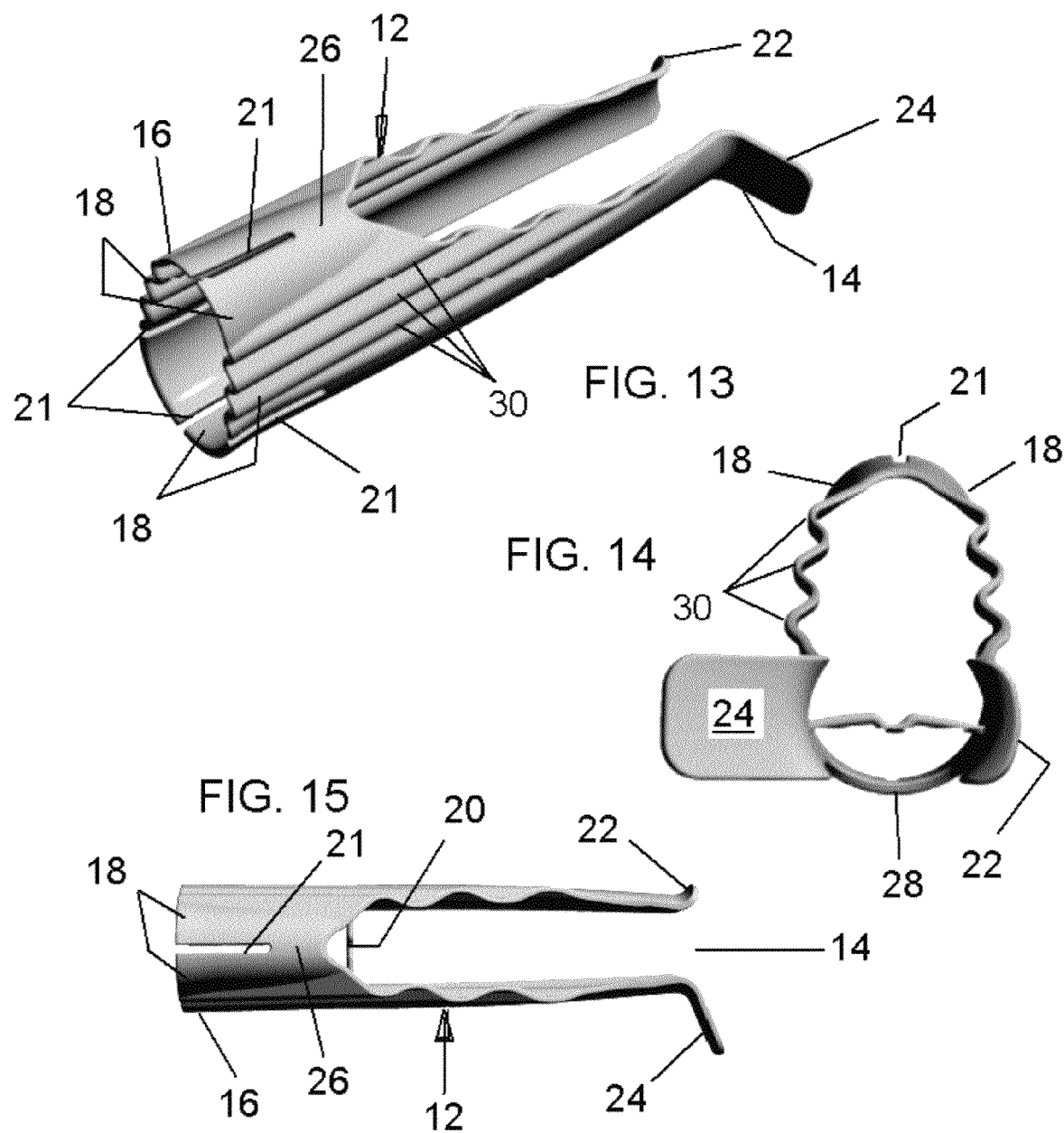

LEEP SAFETY GUARD

CROSS REFERENCE TO RELATED APPLICATION

The present application claims priority on U.S. Provisional Patent Application No. 61/320,026 filed Apr. 1, 2010 which is incorporated here by reference.

FIELD AND BACKGROUND OF THE INVENTION

The present invention relates generally to the field of LEEP or Loop Electrosurgical Excision Procedures, and in particular to a new and useful guard and guide for such procedures and other procedures involving the use of a probe handle.

The American Cancer Society estimates 11,270 new cases of cervical cancer in the United States in 2009, with 4,070 deaths from the disease (1). Most cervical cancer can be prevented. Widespread screening of cervical cytology with the Papanicolaou smear (Pap smear) allows early identification of pre-invasive lesions and the ability to triage patients for further evaluation. In this procedure a sample of cells is collected from the cervix and spread on a slide for cytological evaluation. Current American College of Obstetricians and Gynecologists (ACOG) guidelines recommend initiating cervical cancer screening at age 21 years with a Pap smear and continuing every two years till age 29 (2). Women aged 30 years and older without risk factors may extend the interval to every three years (2). Fifty to sixty million women in the United States have a Pap smear each year. Three to five million women in the United States have an abnormal result.

The Bethesda System for reporting the results of cervical cytology was developed as a uniform system of terminology that would provide clear guidance for clinical management (3). The nomenclature consists of "negative for intraepithelial lesion or malignancy" for slides with no cytological evidence of neoplasia. Alternatively slides with abnormalities are categorized into "atypical squamous cells (ASC), atypical glandular cells (AGC), low grade squamous intraepithelial lesions (LSIL), high grade squamous intraepithelial lesions (HSIL) or squamous carcinoma." Each patient with slides displaying cytologic abnormalities must be evaluated by the care provider for subsequent management and further workup. The American Society for Colposcopy and Cervical Evaluation (ASCCP) provides guidelines for management of cytologic cervical abnormalities (4). As cytology is typically reflective of a cellular process not visible to the naked eye, further evaluation is often recommended with colposcopy. Colposcopy is a medical diagnostic procedure that offers an illuminated magnified view of the cervix and tissues of the vagina and vulva. Pre-invasive lesions are visually distinguished by specific characteristics by a trained colposcopist. Abnormalities are highlighted by the application of acetic acid and/or Lugols solution. The colposcopist obtains biopsies of any abnormal areas for histologic confirmation prior to any treatment intervention.

Histologic classification is a two tiered system that designates CIN (cervical intraepithelial neoplasia) 1 as referring to low grade lesions and CIN 2, 3 to high grade precursors (5). ASCCP provides guidelines for the management and treatment of these histologic lesions (5). Depending on the exact diagnosis and clinical context, recommended treatment may be either excision or ablation, or excision alone. Excisional methods that provide a tissue specimen for pathologic review include cold knife conization, laser conization, electrosurgical needle conization or loop electrosurgical excision procedures (LEEP).

To practice LEEP procedure, first an insulated bivalve speculum is placed in the vagina and the cervix is isolated. Then the diseased cells are identified with specific solutions. Once highlighted (FIGS. 1 and 2), the cellular pathology is excised using an a thin low voltage electrified wire loop shown in FIG. 3. In cutting mode the high frequency current is produced in a smooth uninterrupted sine wave. As the loop is applied to the cervical tissue an arc occurs near the point of contact and the cells rapidly heat and explode into steam. The steam envelope allows for continued arcing, extending the cut with little coagulation artifact. In coagulation mode tissue is fulgurated with shorts bursts of high peak voltage current. Typically both modalities are combined in a blend mode. The procedure lends itself to ease of use in an office setting. Local anesthesia is typically administered, although in certain situations a more monitored operative setting with general anesthesia may be preferred.

A variety of wire loops are available to choose from in order to tailor the specimen to the anatomy of the patient and the characteristics of the lesion. A loop should be chosen that allows excision of the transformation zone to an adequate depth without contact to the vaginal side wall. The loop is attached to a pencil like base that is controlled with a foot switch. Current is applied as the loop contacts the cervix and the specimen is excised. An additional endocervical specimen may be excised as necessary. The excision bed is then commonly fulgurated to reduce bleeding.

A recent analysis shows LEEP to be cost-effective (6). That together with ease of use accounts for its rising popularity in the United States. Women treated with loop excision are likely to convert to Human Papillomavirus (HPV) negative status, which eliminates the risk for H PV-related cervical dysplasia and cancer. The survival rate for properly treated early-stage cervical cancers is between 70 percent and 100 percent. Any device that simplifies the safe and effective use of LEEP in the office setting would have the potential for widespread use.

REFERENCES (1) American Cancer Society. Cancer facts and figures 2009. Atlanta (Ga.): ACS; 2009. Available at: http://www.cancer.org/downloads/STT.

(2) ACOG Practice Bulletin Number 109, December 2009.

(3) Solomon D, et al. The 2001 Bethesda System. JAMA 2002; 287 (16).

(4) Wright T C et al. 2006 consensus guidelines for the management of women with abnormal cervical cancer screening tests. AJOG 2007; 197: 346-355.

(5) Wright T C et al. 2006 consensus guidelines for the management of women with cervical intraepithelial neoplasia or adenocarcinoma in situ. AJOG 2007; 340-344.

(6) Kleinberg M J et al. A cost-effectiveness analysis of management strategies for cervical intraepithelial neoplasia grades 2 and 3. AJOG 2003; 188(5):1186-1188.

U.S. Pat. No. 5,063,908 discloses a vaginal retractor. U.S. Pat. No. 5,916,150 discloses an ear speculum and guide. U.S. Pat. No. 5,394,863 discloses a vaginal fornix illuminator. U.S. Pat. No. 5,846,249 discloses a video speculum. U.S. Pat. No. 6,379,299 discloses a vaginal speculum with adjustable blades.

Also see U.S. Pat. Nos. 6,902,530 Vaginal speculum cover; 6,712,761 Combination of a vaginal speculum with a single-lens colposcope; 6,432,048 Lateral wall retractor vaginal speculum; 6,394,950 Surgical instrument; 6,364,832 Vaginal lateral walls retractor for use in combination with vaginal specula and method of performing vaginal/cervical examination; 6,302,853 Method and apparatus for sampling cervical tissue; 6,280,379 Speculum; 6,258,024 Speculum device; 6,120,438 Posterior vaginal retractor for vaginal surgery or procedure; 6,036,638 Vaginal sleeve; 5,716,329 Disposable expandable speculum; 5,392,764 Gynecological speculum; 5,167,222 Instrument set for operating on the uterus; 3,870,036 Improved speculum barrel member; 2,672,859 in class 600/205, 600/220 and 604/106; 2,579,849 in class 600/215 and 600/220; and 471,647 in class 604/104 and 604/39.

While LEEP is a remarkably common office procedure, there is no equipment for helping guide the loop on its long handle nor for protecting the vagina walls against inadvertently being touched by the loop. There are lateral wall retractors, but nothing that helps stabilize a loop electrode simultaneously. There are loop electrodes with set parameters for a biopsy site that allow for stabilization, but the stick handle is still without support. Also, a standard shape biopsy is ineffective because each cervix and area of disease is unique. In addition, these specific loops are not compatible with standard loops found in all offices. Some standard structures and shown in such patents are U.S. Pat. No. 5,554,159 for an instrument for electro-surgical excisor for the transformation zone of the uterine cervix and method of using same; U.S. Pat. No. 5,324,288 for an electrosurgical loop with a depth gauge; U.S. Pat. No. 5,676,663 for a cone biopsy instrument; and U.S. Pat. No. 3,943,916 for a surgical instrument for conization of the cervix.

A serious drawback of the LEEP procedure thus lies in the danger of using an electrical current within the cave of the vascular delicate vaginal wall and fornix of the cervix as shown in FIGS. 1 and 3. The fornix is defined as the annular recess around the outside of the cervix. Patients as shown in FIG. 2, are awake during the procedure and numbed with local anesthetic. Very often they will jump from the noise of the machine or anxiety. On many occasions the patents' sidewalls have been burned. Patients have been taken to the emergency room due to profuse bleeding and pain from damage to the vaginal wall. In addition, the anatomical location of the cervix deep within the vagina necessitates the use of a long electrode. This creates instability and it is nearly impossible to eliminate some sort of tremor from the practitioner's hand.

The success of this procedure is dependent on the accuracy of excising complete margins, and loss of control can cause patient harm, as well as imprecision but to date there has been not mechanism for preventing this serious drawback.

SUMMARY OF THE INVENTION

It is an object of the present invention to solve the aforementioned problems by providing a generally cylindrical sleeve of flexible, preferably transparent material that slides easily through the placed speculum. At the far or inner end of the sleeve a cervical guard is provided, such as a plurality of cervical panels evolved from the sleeve or movably slidable with respect to the sleeve, to embrace the cervical tissue, for protecting the friable posterior vaginal walls and fornix.

Accordingly, another object of the present invention is to provide a guard and guide apparatus and method for use with a speculum having jaws in a vagina to define a passage toward a cervix at an end of the vagina, the apparatus including a guard body that is movable into the speculum passage, the guard body having sides, a top and a bottom defining a tunnel toward the cervix for preventing contact between a probe, e.g. a LEEP probe, and walls of the vagina. Flexible cervix panels are mounted to the guard body and extend or are extendable toward the fornix of the cervix for covering the fornix to protect it from inadvertent contact by the probe. A support fulcrum is connected to the guard body and extends in the tunnel at a location between inner and outer ends of the guard body for supporting the probe handle to help a practitioner steady the probe handle and aim the probe accurately to a selected location on the cervix for performing the LEEP process or for other procedures.

Although the present invention is particularly suited to improving LEEP, it can also be used for any other process requiring an elongated probe handle having a probe or other functional mechanism at its inner end that must be accurately placed in a patient. Other potential uses for the invention are, but are not limited too, placement of a foley balloon for induction of labor, cerclage placement for cervical insufficiency, and repair of cervical laceration. Any cervical procedures requiring precision and retraction will benefit from the invention.

A further object of the present invention is to provide the practitioner with a guide or support fulcrum for the probe handle or stick, for example in the form of a U-shaped metal or other strong material structure inside the guard on which the stick can be supported but freely pivoted and guided to execute the procedure accurately without allowing the hot loop or other probe or functional end from inadvertently swinging against the vaginal walls or onto locations on the cervix other than the locations to be treated.

In a further embodiment of the invention, at a location approximately 3 cm distal i.e. outside the inner end of the guard, an aiming eye, sighting aperture or further pivot hole can be provide that the electrode stick slides through. This allows for a full range of axial motion, yet further stabilizes the probe and its handle and eliminates any natural tremor while the encompassing sleeve protects the side walls of the vagina during insertion and removal of the hot loop or probe.

Another embodiment of the invention comprises a bivalve expandable rectangular or cylindrical sleeve that easily slides into a LEEP speculum. At the far end of the device are flexible extensions on the superior and posterior distal ends. These extensions or cervical panels can follow the contour of the cervix. There are also extendable side walls that elongate to encompass the side of the cervix and protect the fornix. In addition there is a mid-sleeve adjustable pivot or aiming fulcrum that the probe handle rests on as in other embodiments of the invention. This allows for a full range of motions and stabilizes and eliminates any natural tremor. The apparatus is preferably made of non-conductible material that protects the side walls of the vagina during insertion and removal of the hot loop or probe.

The speculum protective guide of the invention allows for protection of the fornix as well as lateral vaginal walls and includes a stabilizing pivot or support fulcrum to allow for more accurate fine movement. In addition, it is completely adjustable to all women's anatomy standard loops and speculums.

A further advantage of the invention is that it is compatible with all standard loops that currently exist as well as the speculum so that offices would be able to integrate the instrument without making their current equipment obsolete.

A restriction of the material of the device is that it is non-conductible in view of the exposed loop that carried electrical current. It could be either reusable or disposable depending on which makes more practical production sense.

While the safety features of the design are paramount, the manageability of the design allows the beginning surgeon to perform like an expert.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 5 is a perspective view of the guard/guide of the embodiment of FIG. 4, in an open position before it is inserted into a speculum for use during a LEEP and in preparation for receiving the stick handle of the LEEP loop;

FIG. 6 is an exploded view of the parts used to assemble the invention of FIG. 4;

FIG. 7 is a perspective view of the guard/guide of the invention of FIG. 4, in a closed and retracted position it would take inside the speculum in the vagina of a patient during a LEEP;

FIG. 8 is a perspective view of the guard/guide of the invention of FIG. 4, in a closed and extended position it would take inside the speculum in the vagina of a patient during a LEEP;

FIG. 9 is a transverse sectional view of the guard/guide of FIGS. 7 and 8 looking toward the patient's cervix and with the LEEP handle resting on a guiding fulcrum support of the invention;

FIG. 10 is a side sectional view of a patient's vagina being treated using a LEEP probe, the vaginal walls spread and being held open using a known speculum and with another embodiment of the invention in place to protect the vaginal wall tissues and around portions of the cervix that are not to the resected;

FIG. 11 is a perspective view of another embodiment of the invention;

FIG. 12 is a perspective view of a still further embodiment of the invention;

FIG. 13 is a perspective view of another embodiment of the invention;

FIG. 14 is rear elevational view of the embodiment of FIG. 13;

FIG. 15 is a top plan view thereof;

DESCRIPTION OF THE PREFERRED EMBODIMENTS

Figure 1:
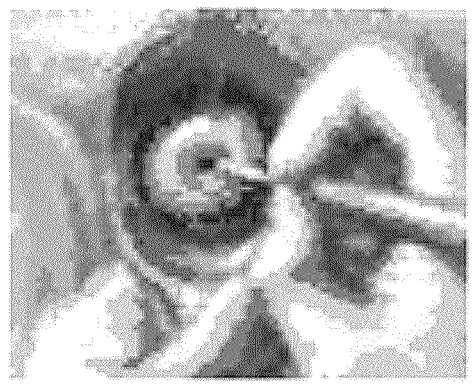
FIG. 1 is a view looking into the vagina of a patient being treated using a LEEP with the vaginal walls being spread using a known speculum, but still in danger of being touched by the LEEP loop.
Figure 2:
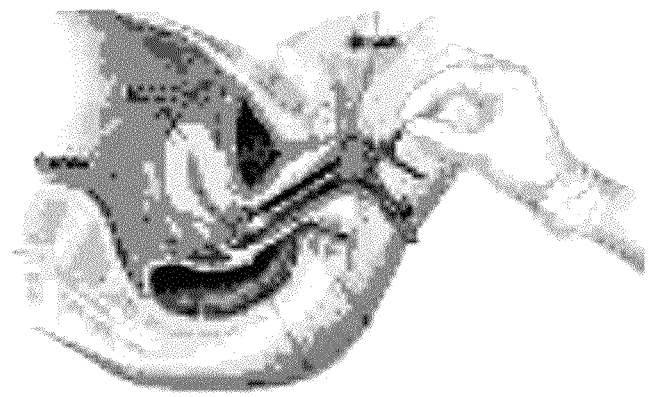
FIG. 2 is a side sectional view of a patient being treated using a LEEP with the vaginal walls spread using the known speculum.
Figure 3:
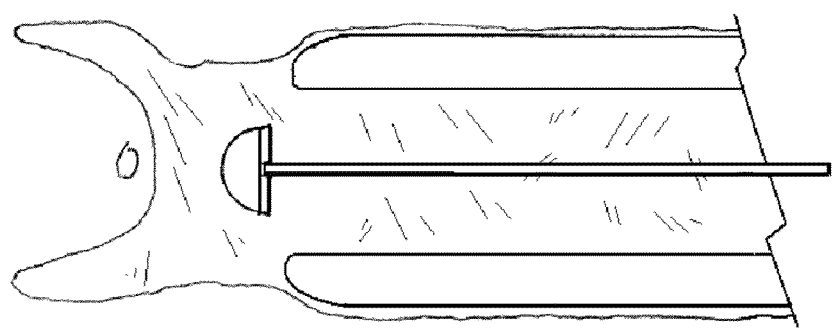
FIG. 3 is an enlarged sectional view of the patients vagina and cervix with the LEEP loop about to resect tissue from the cervix.

Referring now to the drawings, in which like reference numerals are used to refer to the same or functionally similar elements, FIGS. 4 to 9 illustrate a vaginal wall and cervix guard and probe handle guide apparatus 10 for use with a speculum 100 having an upper or superior jaw 102 and a lower or inferior jaw 104, in a vagina and defining an access passage between the jaws to a cervix having a fornix at an end of the vagina. The bivalve apparatus 10 of this embodiment of the invention comprises a guard body 12 movable into the passage between the jaws 102, 104 of the speculum 100. The guard body 12 has sides, a top and a bottom defining a probe handle tunnel in the vagina, extending toward the cervix for preventing contact between a probe 106 at an end of the probe handle 108 and walls of the vagina. The guard body 12 has an outer end 14 with a guard handle to be held be a practitioner for moving the guard body 12 into the passage toward the cervix.

A plurality, in this case, two flexible cervix panels 18, 18, are mounted to the guard body 12 and extend from an inner end 16 of the guard body 12 for extending toward the fornix of the cervix for covering at least portions of the cervix to protect the cervix from contact by the probe 106. A support fulcrum 20 is connected to the guard body 12 and extends in the tunnel at a location between the inner and outer ends of the guard body 12, for supporting the probe handle 108 to help a practitioner holding the probe handle, aim the probe 106 accurately to a selected location on the cervix to be resected.

In the embodiment of FIGS. 4 to 9, as well as that of FIG. 11, the guard body 12 is a separate piece of flexible material from each of the cervix panels 18. The cervix panels 18 each having a panel handle 22 near the outer end 14 of the guard body 12, and are each movably mounted to the guard body 12 for being independently movable toward the cervix from movement of the guard body itself. In this way the guard body can be separately and accurately placed in the vagina, independently of the cervix panels.

In the embodiment of FIGS. 4 to 9, the guard body comprises upper and lower substantially U-shaped guard portions 12a and 12b that are at least partly nested with each other, the guard portions being pivotally connected to each other near the outer end of the guard body at a pair of pivot axes 24. One of the guard portions, e.g. the lower one 12b, is upwardly open an the other guard portion 12a is downwardly open to form the tunnel, the one portions 12b being an inner guard portion that is at least partly covered by the other guard portion 12a. The support fulcrum 20 is connected inside the inner guard portion 12b.

Figure 4:
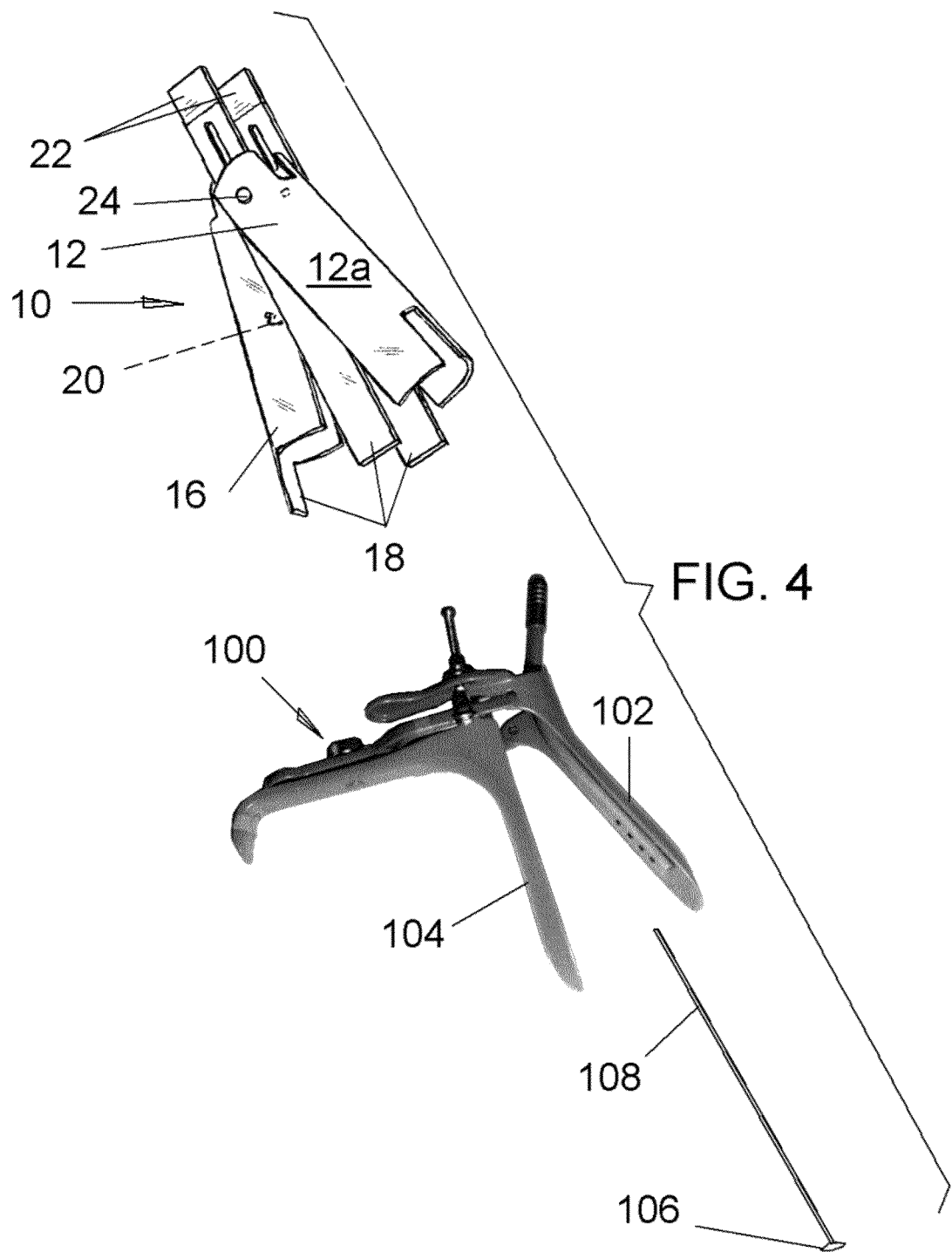
FIG. 4 is an exploded view of one embodiment of the vaginal wall guard and loop guide of the invention in the form of a bivalve apparatus.
Figure 16:
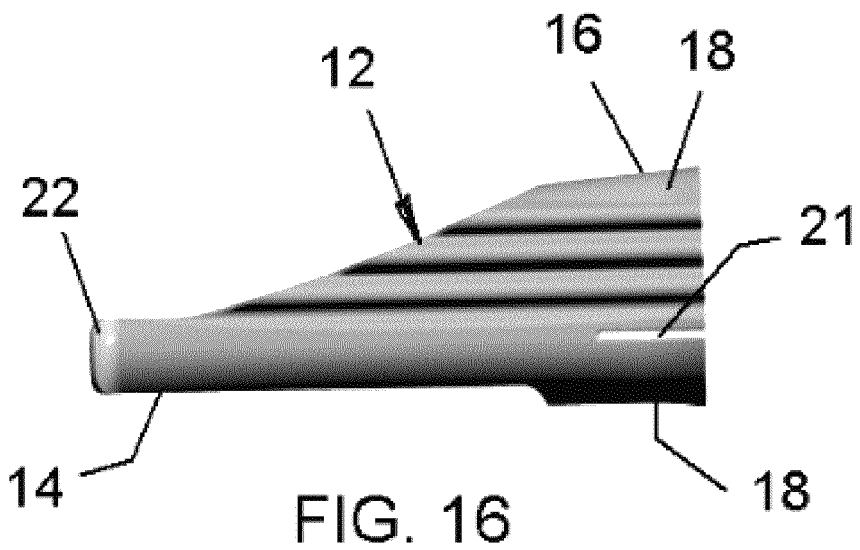
FIG. 16 is a side elevational view thereof.
Figure 17:
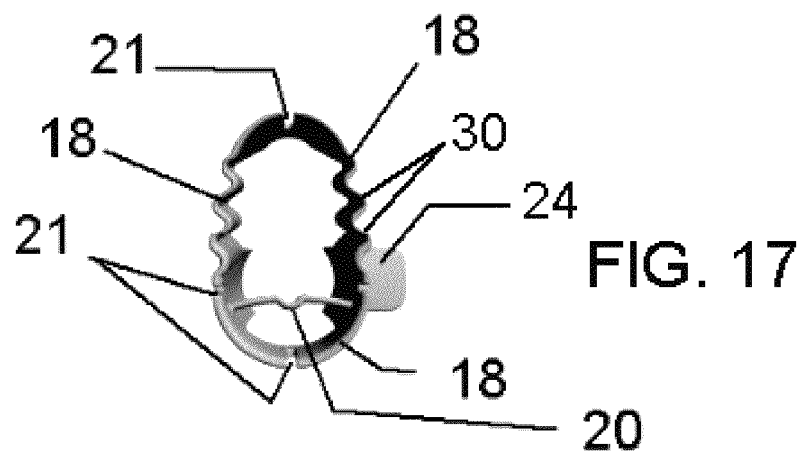
FIG. 17 is a front elevational view thereof.
Figure 18:
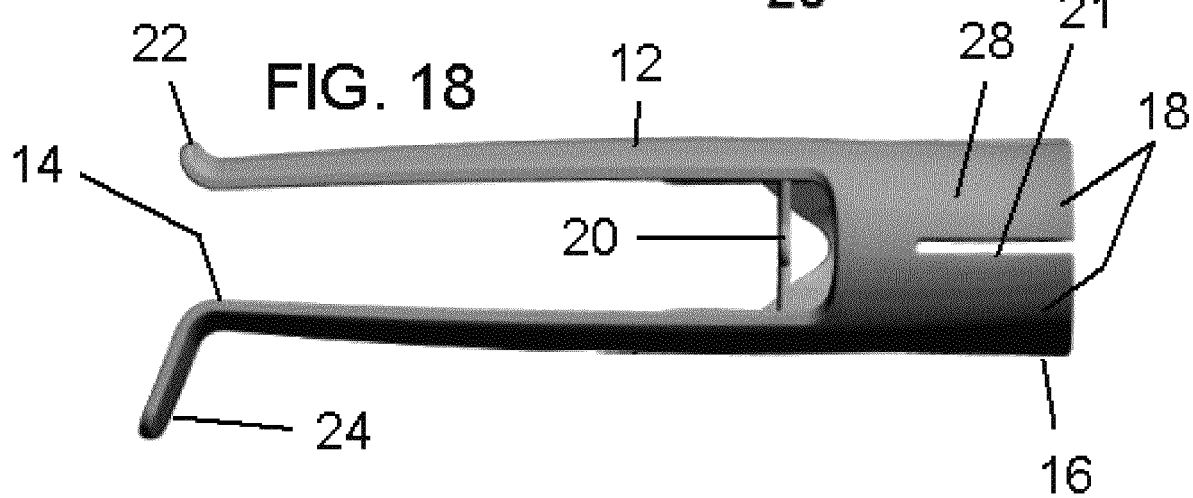
FIG. 18 is a bottom plan view thereof.

Biasing means such as a V-shaped spring 26 is engaged between the guard portions 12a and 12b for urging the inner ends 16 of the guard portions to pivot away from each other and toward the vaginal walls. This open or spread position is shown in FIGS. 4 and 5. The cervix panels 18 each comprise an elongated panel slidably mounted to the respective pivot axes 24 by slots 28 in each panel, for movement toward the cervix.

For better visibility of the vaginal and cervix tissued to the practitioner, the guard body and cervix panels comprise transparent plastic material, for example made of any of: poly (vinyl chloride); poly(styrene); poly(methyl methacrylate); poly(carbonate); poly(urethane); or copolymers or mixtures thereof, or any other suitable material.

In the embodiment of FIG. 10, the guard body 12 and the cervix panels 18 are made of one piece of flexible material, e.g. silicone, with the cervix panels 18 comprising a plurality of substantially rectangular panels connect to and extending outwardly from the inner end 16 of the guard body 12. FIG. 10 also shows the relationship of the guard/guide apparatus 10 of the invention, inside the speculum 100, between is jaws 102, 104, and the cervix 120 and the fornix 122, as well as the vaginal walls 124. All embodiments of the invention are positioned in the same way.

In the embodiment of FIG. 11, the guard body 12 is a separate piece of flexible material from the cervix panels 18, the cervix panels having one panel handle 22 at the outer end 14 of the apparatus, and being movably mounted together the guard body 12 for being independently movable toward the cervix from movement of the guard body.

FIG. 12 illustrates a variation of the one piece guard body 12 and cervix panels 18 that includes not only the fulcrum 20 but also a sighting aperture 30 connected to the guard body 12 and in the tunnel between the outer handle end 14 of the guard body 12 and the support fulcrum 20, for receiving the probe handle to further aid in aiming the probe to a selected location on the cervix. This sighting aperture 30 can also be included in the other embodiments of the invention and, like the support fulcrum 20, can be made of insulated metal or plastic wire fastened at its opposite ends to the adjacent walls of the guard body or portion thereof.

Referring now to FIGS. 13 to 18, a still further embodiment of the invention is illustrated. As with the embodiment of FIG. 12, the embodiment of FIGS. 13 to 18 is a one piece elastomer structure. The guard body 12 has four cervix panels 18 formed by four short, circumferentially spaced and axially extending slots 21 in the inner end 16 of the guard body 12. Guard body 12 also includes a fulcrum 20 in the tunnel between an outer handle end 14 of the guard body 12 and its inner end 16, with a downwardly concave arcuate portion at least at its center for receiving and supporting a probe handle to aid in the supporting and aiming of a probe to a selected location on the cervix. The support fulcrum 20 in FIGS. 13 to 18 is made of insulated metal wire or plastic wire fastened at its opposite ends to the adjacent walls of the guard body 12, or is formed as part of the elastomer guard body 12.

The one piece guard body 12 of FIG. 13 can be made, for example, of any of: silicone rubber, poly(vinyl chloride); poly(styrene); poly(methyl methacrylate); poly(carbonate); poly(urethane); or copolymers or mixtures thereof, or any other suitable, flexible and self-supporting elastomer material. The support fulcrum 20 can be make of the same material or of different stronger material like metal wire encased in one of these elastomer materials.

As noted, the guard body 12 with its cervix panels 18 are made of one piece of flexible material, the cervix panels being a plurality of flexible panels that are separated by circumferentially spaced axially extending slots 21 in the inner end 16 of the guard body 12. The guard handle at the outer end 14 of the guard body have a shorter radial handle extension 22 from one side, and a longer radial handle extension 24 from an opposite side of the outer end 14 of the guard body 12. The top 26 and the bottom 28 of the guard body 12 are shorter than the sides of the guard body and are adjacent the axially extending slots 21 in the inner end 16 of the guard body, that is, closer to the inner end 16 than to the outer end 14 of the guard body 12. The sides also having axially extending and circumferentially spaced flutes 30 for increasing vertical flexible expansion and contraction of the guard body 12.

In use a practitioner inserts the guard body 12 between the jaws of a speculum after the speculum has been inserted into the patient's vagina, and at a location that is far enough back so that the practitioner has assess to the handles 22 and 24 of the guard. Alternatively the guard body 12 is first inserted into the speculum and then the speculum is inserted into the vagina. Using the handles 22 and 24, the practitioner than maneuvers the panels 18 over the cervix. Since the one piece guard body 12 is made of flexible material, the panels with bend out and around the cervix to shield it from the probe that is next inserted into the guard body tunnel so that its handle will rest of the support fulcrum 20.

The apparatus and method of the invention can also be used for any vaginal/cervical procedure that requires exposure, for example inserting Foley balloons for induction of labor, placing cerclages for cervical insufficiency, repairing cervical lacerations after vaginal deliveries, etc. The manipulating portion of the devices for any and all of these procedures is called a probe handle for the purpose of this disclosure.

While specific embodiments of the invention have been shown and described in detail to illustrate the application of the principles of the invention, it will be understood that the invention may be embodied otherwise without departing from such principles.

What is claimed is:
1. A LEEP arrangement, the arrangement comprising:
a vaginal wall and cervix guard and probe handle guide apparatus for use in a vagina and defining an access passage to a cervix having a fornix at an end of the vagina, the apparatus comprising:
a guard body movable into the vagina, the guard body having sides, a top and a bottom defining a probe handle tunnel in the vagina extending toward the cervix for preventing contact between a probe at an end of the probe handle and walls of the vagina, the guard body having an outer end with at least one guard handle to be held by a practitioner for moving the guard body into the passage toward the cervix, and an inner end;
the guard body comprising a plurality of flexible cervix panels at the far the inner end of the guard body for extending toward the fornix of the cervix for covering at least portions of the cervix to protect the cervix from contact by the probe; and
a support fulcrum connected to the guard body and extending in the tunnel at a location between the inner and outer ends of the guard body for supporting the probe handle to help a practitioner holding the probe handle aim the probe accurately to a selected location on the cervix;
the guard body including the cervix panels being made of one piece of flexible material, the cervix panels comprising a plurality of flexible panels that are separated by circumferentially spaced axially extending slots in the inner end of the guard body, all of the slots being empty notches in said one piece of flexible material, the cervix panels and the slots both beginning at the far inner end of the guard body and only extending a portion of the distance from the inner end of the guard body to the guard handle at the outer end of the guard body;
wherein the slots allow the flexible cervix panels to bend radially outwards and away from each other to conform to the shape of each cervix, the cervix panels at the inner end of the guard body being adapted to bend independently of the other portions of the guard body in response to being pressed against a cervix;
wherein the LEEP arrangement has an operable state being positioned within a female patient with the inner end of the guard body positioned at the patient's cervix;
wherein when in said operable state at least some of the cervix panels are radially flexed with respect to the axis of the arrangement to contour to the shape of the cervix;
the arrangement further comprising a probe handle removably resting on the support fulcrum, the probe handle being attached to a wire loop carrying an electrical current; the wire loop being for contacting the cervix to thereby excise tissue in the operable state.

2. The LEEP arrangement of claim 1, wherein the guard handle at the outer end of the guard body has a shorter radial handle extension from one side and a longer radial handle extension from an opposite side of the guard body.

3. The LEEP arrangement of claim 1, wherein the guard handle at the outer end of the guard body has a shorter radial handle extension from one side and a longer radial handle extension from an opposite side of the guard body, the top and bottom of the guard body being shorter than the sides of the guard body and being adjacent the axially extending slots in the inner end of the guard body.

4. The LEEP arrangement of claim 1, wherein the guard handle at the outer end of the guard body has a shorter radial handle extension from one side and a longer radial handle extension from an opposite side of the guard body, the top and bottom of the guard body being shorter than the sides of the guard body and being adjacent the axially extending slots in the inner end of the guard body, the sides having axially extending and circumferentially spaced flutes for increasing vertical flexible expansion and contraction of the guard body.

5. The LEEP arrangement of claim 1, the guard body comprising four flexible cervix panels and four circumferentially spaced axially extending slots in the inner end of the guard body between the cervix panels.

6. The LEEP arrangement of claim 1, the guard body comprising four flexible cervix panels and four circumferentially spaced axially extending slots in the inner end of the guard body; wherein two of the cervix panels comprise flexible accordion-like sections which allow the panels to expand and contract vertically.

7. The LEEP arrangement of claim 1, wherein the support fulcrum comprises a downwardly concave portion for removably receiving and supporting a probe handle.

8. The LEEP arrangement of claim 1, wherein the guard body comprises an unbroken, substantially tubular, continuous cross-section of the unitary piece of flexible material located axially between the slots and cervix panels towards the inner end, and the at least one guard handle on the opposite outer end.

9. The LEEP arrangement of claim 1, wherein the support fulcrum of the apparatus is adapted for interchangeably supporting a plurality of different probes for use by the practitioner by allowing the practitioner to temporarily rest probe handles on the support fulcrum.

10. The LEEP arrangement of claim 1, wherein the flexible cervix panels automatically resiliently return to an unbent position when they are removed from against the cervix.

11. The LEEP arrangement of claim 1, wherein the guard body and cervix panels comprise transparent plastic material.

12. The LEEP arrangement of claim 1, wherein the guard body and cervix panels comprise transparent plastic material selected from the group consisting of: silicone rubber, poly (vinyl chloride); poly(styrene); poly(methyl methacrylate); poly(carbonate); poly(urethane); and copolymers and mixtures thereof.

* * * * *